United States Patent
Stark

(10) Patent No.: US 6,639,220 B2
(45) Date of Patent: Oct. 28, 2003

(54) DATA REDUCER FOR A SCINTILLATION CAMERA

(75) Inventor: Iain Stark, Nepean (CA)

(73) Assignee: Is² Research Inc. (CA)

( * ) Notice: Subject to any disclaimer, the term of this patent is extended or adjusted under 35 U.S.C. 154(b) by 74 days.

(21) Appl. No.: 09/931,169

(22) Filed: Aug. 17, 2001

(65) Prior Publication Data

US 2002/0036268 A1 Mar. 28, 2002

Related U.S. Application Data

(63) Continuation of application No. 09/127,988, filed on Aug. 3, 1998, now abandoned.

(30) Foreign Application Priority Data

Aug. 1, 1997 (CA) .............................................. 2212196

(51) Int. Cl.⁷ .............................................. G01T 1/164
(52) U.S. Cl. .............................. 250/363.02; 250/363.08
(58) Field of Search ...................... 250/363.02, 363.08, 250/366

(56) References Cited

U.S. PATENT DOCUMENTS

| | | | |
|---|---|---|---|
| 3,011,057 A | 11/1961 | Anger | 250/71.5 |
| 3,171,763 A | 3/1965 | Tanaka | 148/185 |
| 3,914,611 A | 10/1975 | Stout | 250/366 |
| 4,060,730 A | 11/1977 | Zioni et al. | 250/369 |
| 4,497,024 A | 1/1985 | Roth | 364/414 |
| 4,780,823 A | 10/1988 | Stoub et al. | 364/413.13 |
| 4,857,722 A | 8/1989 | Kumazawa et al. | 250/207 |
| 4,860,205 A | 8/1989 | Jatteau | 364/413.24 |
| 4,879,464 A | 11/1989 | Iinuma | 250/361 |
| 4,881,171 A | 11/1989 | Jatteau et al. | 364/413.24 |
| 4,900,931 A | 2/1990 | Tournier et al. | 250/369 |
| 5,285,072 A | 2/1994 | Klingenbeck-Regn et al. | 250/369 |
| 5,309,357 A | 5/1994 | Stark et al. | 364/413.24 |
| 5,504,334 A | 4/1996 | Jansen et al. | 250/369 |

FOREIGN PATENT DOCUMENTS

| | | |
|---|---|---|
| CA | 1280244 | 2/1991 |
| EP | 0 450 388 B1 | 10/1991 |
| EP | 0 531 566 B1 | 3/1993 |
| GB | 2 253 274 A | 9/1992 |

Primary Examiner—Constantine Hannaher
Assistant Examiner—Otilia Gabor
(74) Attorney, Agent, or Firm—Finnegan, Henderson, Farabow, Garrett & Dunner, LLP

(57) ABSTRACT

A method of reducing data in a scintillation camera having a plurality of photomultiplier tubes arranged in rows and columns. The method comprises steps of (a) summing output signals from the photomultiplier tubes of each row to provide a summed row signal for each row, (b) summing output signals from the photomultiplier tubes of each column to provide a summed column signal for each column, (c) selecting a largest summed row signal and a largest summed column signal from the summed row and column signals, and (d) determining at least three output signals to be required for computing the location of a scintillation event by using the largest summed row and summed column signals, whereby reducing the amount of data to be processed. The determining step can comprise steps of locating an X and Y coordinate corresponding to the largest summed row and summed column signals, and choosing the output signals from at least three photomultiplier tubes which surround the X and Y coordinate.

8 Claims, 14 Drawing Sheets

DATA REDUCER FOR A SCINTILLATION CAMERA

This is a continuation of application Ser. No. 09/127,988 filed Aug. 3, 1998 which is incorporated herein by reference, now abandoned.

FIELD OF INVENTION

The present invention relates to a data reducer for a scintillation camera.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

The detector head of the scintillation camera must be able to pass underneath the patient. Therefore, in order for the scintillation camera to generate images from underneath the patient, the patient support must be thin. However, detector heads are generally supported by a pair of arms which extend from a gantry. Thus, the patient support generally must be cantilevered in order for the detector head to be able to pass underneath the patient without contacting any supporting structure associated with the patient support. The design of a cantilevered patient support that is thin enough to work properly with a scintillation camera is exceedingly difficult. Expensive materials and materials that are difficult to work with, such as carbon fibre, are often used in the design of such cantilevered patient supports.

A certain design of gantry or support structure for a scintillation camera includes a frame upon which a vertically oriented annular support rotates. Extending out from the rotating support is an elongate support. The elongate generally comprises a pair of arms. The pair of arms generally extends through a corresponding pair of apertures in the rotating support. One end of the pair of arms supports the detector head on one side of the annular support. The other end of the pair of arms supports a counter balance weight. Thus, the elongate support is counterbalanced with a counterweight on the opposite side of the detector head.

With such a design of support structure for a scintillation camera, a patient must lie on a horizontally oriented patient support. The patient support must be cantilevered so that the detector head can pass underneath the patient. If the detector head must pass underneath only one end of the patient, such as the patient's head, the cantilevered portion of the patient support is not long enough to cause serious difficulties in the design of the cantilevered patient support. However, if the camera must be able to pass under the entire length of the patient, the entire patient must be supported by the cantilevered portion of the patient support. As the cantilevered portion of the patient support must be thin so as not to interfere with the generation of images by the scintillation camera, serious design difficulties are encountered.

Among the advantages associated with such as design of support structure is that a patient may be partially pass through the orifice defined by the annular support so that the pair of arms need not be as long. However, the patient support must be able to support the patient in this position relative to the annular support, must be accurately positionable relative to the annular support, and must not interfere either with the rotation of the annular support or with the cables which will inevitably extend from the detector head to a nearby computer or other user control.

The photomultiplier tubes in a scintillation camera generate electric signals. The signals are processed, and images are created corresponding to the radiation emitted by the patient.

U.S. Pat. No. 3,011,057 issued to H. O. Anger, discloses a typical scintillation camera of the type described, wherein the photomultiplier are arranged in a hexagonal pattern over a circular crystal, and have overlapping fields of view. A hexagonal pattern is selected because it achieves the densest clustering possible of photomultiplier, having circular or hexagonal photocathodes.

Computation of the displacement of a light event from each of the two orthogonal coordinate axes is achieved by weighting the outputs of each of the photomultipliers in accordance with its distance from the coordinate axis in question, and summing the outputs of photomultipliers. The weighted sum of the photomultiplier signals used to calculate the displacement of a light event from a coordinate axis represent a fixed analytical function of the signals. Because a single analytical function is used for computation purpose irrespective of the location in the crystal of a light event, the two parameters that are measures of the quality of performance of a scintillation camera of the type described, namely spatial resolution and uniformity, are spatially dependent (i.e., are dependent on the location of the light event in the crystal). In other words, the resolution and uniformity for a given analytical function of the photomultiplier signals may be much better for events that occur in one region of the crystal as compared to events that occur in other regions.

Another conventional camera of the type described is disclosed in U.S. Pat. No. 3,171,763 issued to Tanaka et al. In this camera, the coordinate position of a photomultiplier establishes a delay time by which the photomultiplier signals can be separated in time sequence. The maximum resolution and linearity of this camera depend on the similarity between the shape of the electronic pulse and the shape of the waveform produced as a result of geometric configuration of the device. Thus, this detector used time domain as the basis for calculating position and, as a consequence, has a relatively long dead time.

Another conventional camera of this type described is disclosed in U.S. Pat. No. 4,060,730 issued to Zioni et al. This describes a camera in which summed row and column data is used as the basis for computing circuitry coupled via an ADC to the photomultiplier to compute the projection of a light event in the crystal on a reference axis by forming an analytical function of the signals of the photomultipliers according to the spatial location of the light event in the crystal.

One problem to overcome in the design of scintillation cameras is that the computers generally used are not able to process the entirety of the data at the rate that it is generated by the photomultiplier tubes and associated electronic circuitry. It is necessary, therefore, to implement a method to reduce the quantity of data processed by the scintillation camera's computer. In other words, only the useful values generated by the photomultiplier tubes must be selected, that is, the rest of the values are noise and therefore not useful.

Referring to FIG. 13, the signal generated by a photomultiplier tube rises quickly, that is, in about 200 nanoseconds, and decays more slowly, that is, in about 1 microsecond. It is in this short time period that the light signal must be collected. How effectively light is collected during this period is important, because the performance of a scintillation camera is directly related to how completely light is collected. A camera that misses too much light will generally have poor performance. Thus, it is important that the signal selection process does not interfere with the collection of light signal.

One light collection method known in the art is the threshold method. The threshold method is typically set up by assigning to the output an offset below zero volts. Thus, when the signal rises above zero volts, acceptance of the signal begins. However, one disadvantage is that when the signal drops below zero volts again, the signal is no longer accepted. This means that the integral of the signal between the offset voltage and zero volts is lost. The threshold method is slow, has an inherent bandwidth limitation, and distorts the signal.

SUMMARY OF THE INVENTION

An object of the invention is to provide an improved data reducer for a scintillation camera.

A second object of the invention is to provide a data reducer for a scintillation camera that effectively selects signals from photomultiplier tubes while minimizing distortion of the signals. According to one aspect of the present invention, there is provided a method of reducing data in the localization processing of scintillation events in a scintillation camera having a plurality of photomultiplier tubes arranged in rows and columns. The method comprises steps of: summing output signals from the photomultiplier tubes of each row to provide a summed row signal for each row; summing output signals from the photomultiplier tubes of each column to provide a summed column signal for each column; selecting a largest summed row signal and a largest summed column signal from the summed row and column signals; and determining at least three output signals to be required for computing the location of a scintillation event by using the largest summed row and summed column signals, thereby reducing the amount of data to be processed. The determining step can comprise steps of: locating an X and Y coordinate corresponding to the largest summed row and summed column signals; and choosing the output signals from at least three photomultiplier tubes which surround the X and Y coordinate.

In an embodiment of the invention a data reducer for a scintillation camera is applied when photomultiplier tubes in an array thereof generate output signals following a flash of light from a scintillator. The output signal from a given photomultiplier tube is connected to an integrating preamplifier circuit. Each output signal is connected to an analog to digital converter, to a row amplifier circuit and to a column amplifier circuit. The signal from the analog to digital converter is provided via a bus to a data processor. The output signal of the data processor is set according to operational requirements, and then provided to a digital to analog converter. The signal from the row amplifier circuit is provided to a row summing circuit. The signal from the column amplifier circuit is provided to a column summing circuit. The respective signals from the row summing circuit and the column summing circuit are provided to an energy analyser. The energy analyser ensures that the signal is the result of a gamma event. The output of the digital to analog converter is compared with the output of the energy analyser. If the signal from the energy analyser conforms with the requirements of the digital to analog converter, then a valid signal is sent to the photomultiplier tube map and address. From the row summing circuit the largest row signal is sent to the photomultiplier tube map and address, and from the column summing circuit the largest column signal is sent to the photomultiplier tube map and address.

Advantageously, the invention provides: an improved data reducer for a scintillation camera; and a data reducer for a scintillation camera that effectively selects signals from photomultiplier tubes while minimizing distortion of the signals.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

Figure 1:
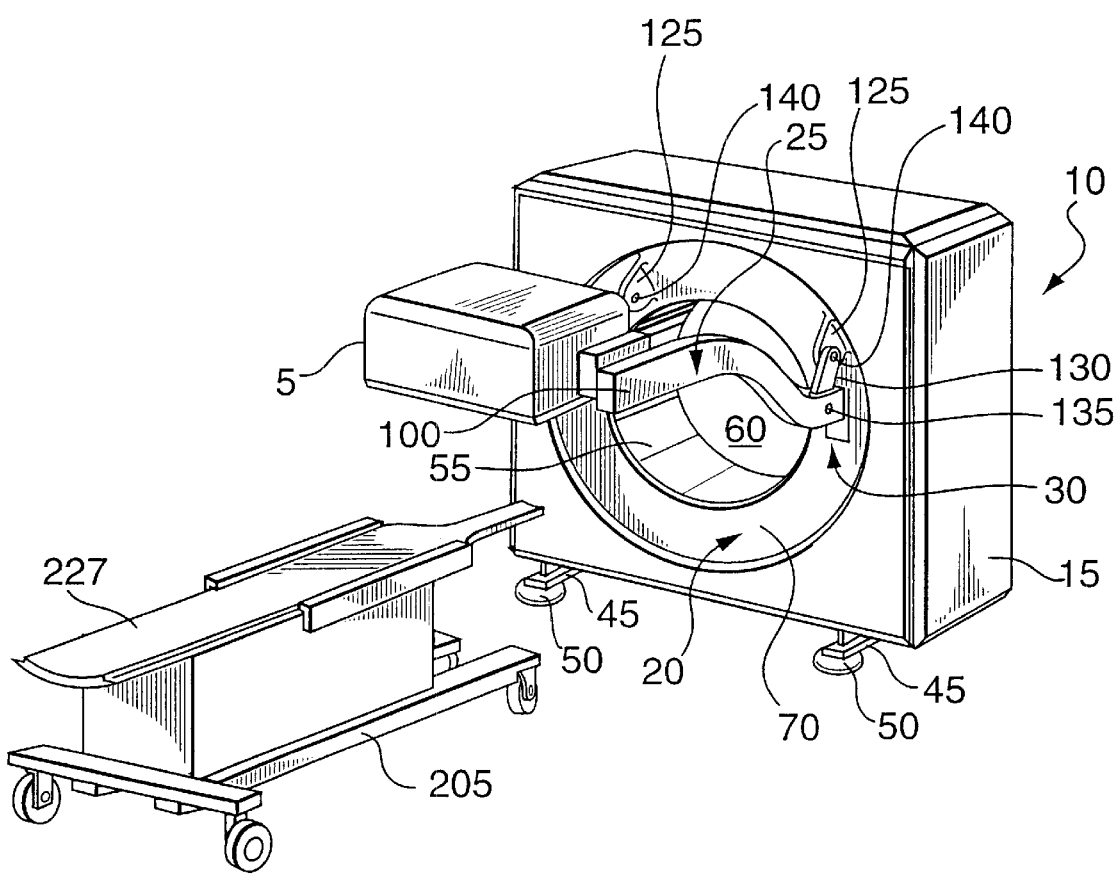
FIG. 1 is a perspective view of a scintillation camera including a detached patient support in accordance with the invention.
Figure 2:
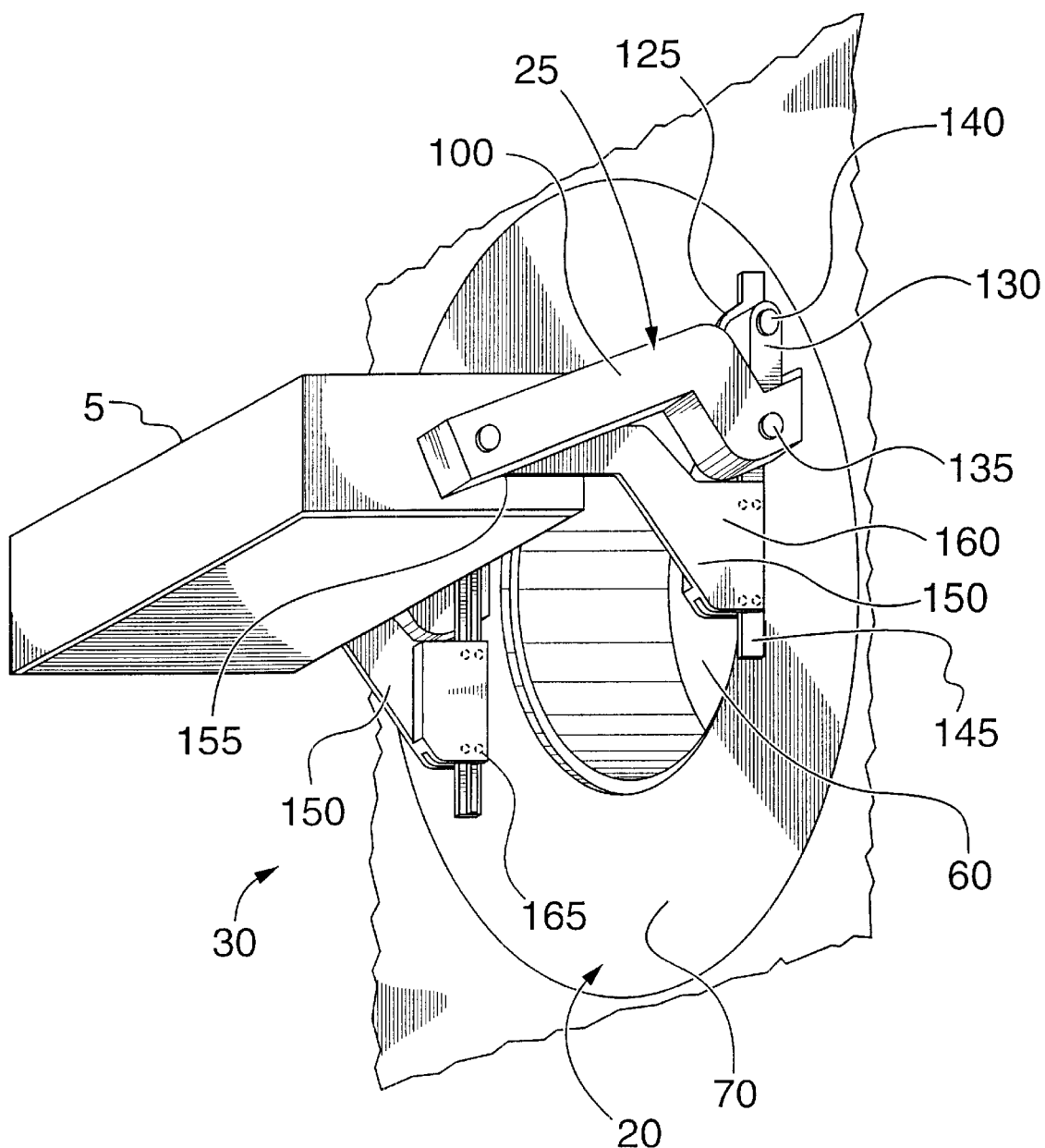
FIG. 2 is a perspective view of the guide of a scintillation camera.
Figure 3:
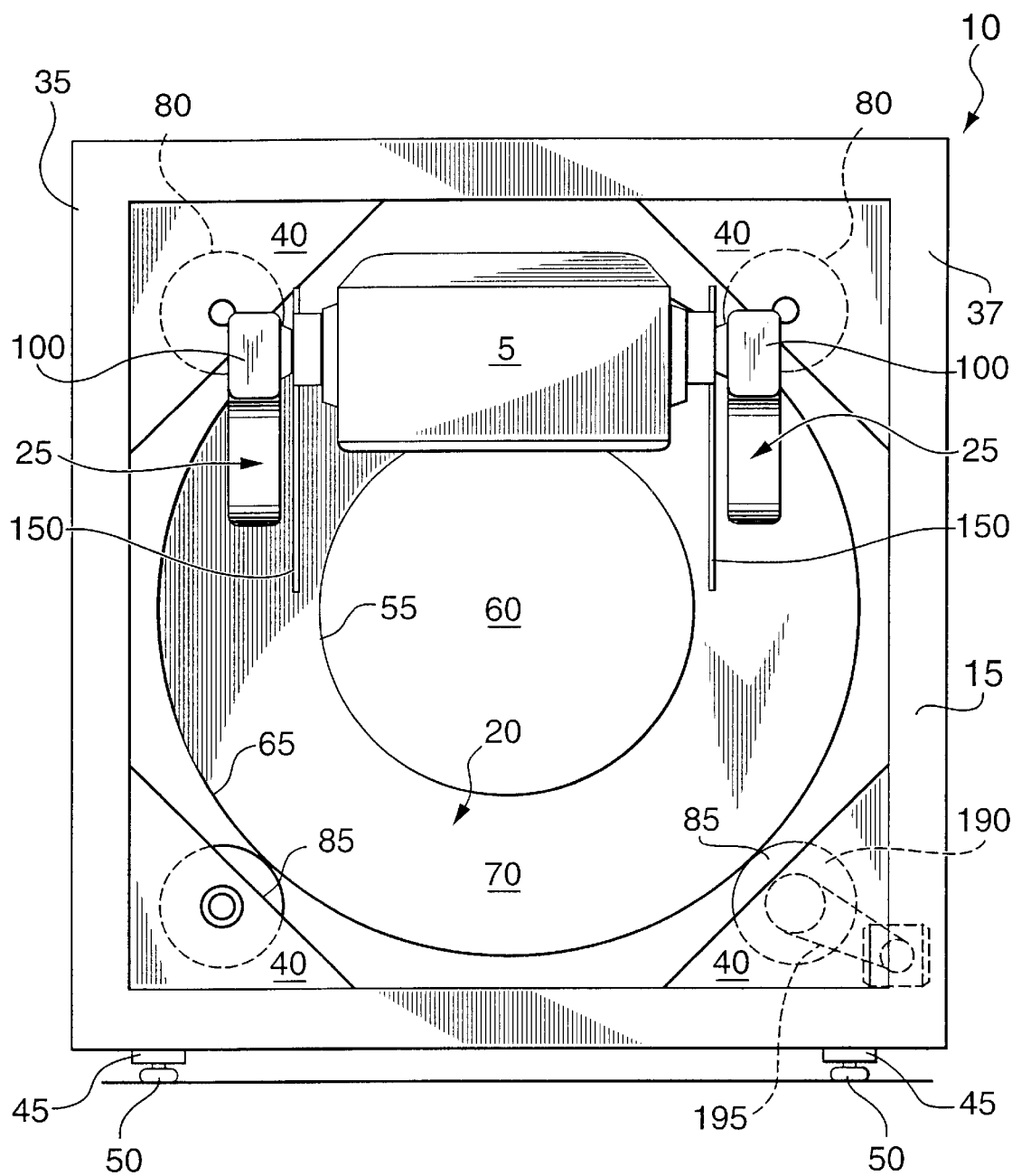
FIG. 3 is a front elevation view of a scintillation camera.
Figure 4:
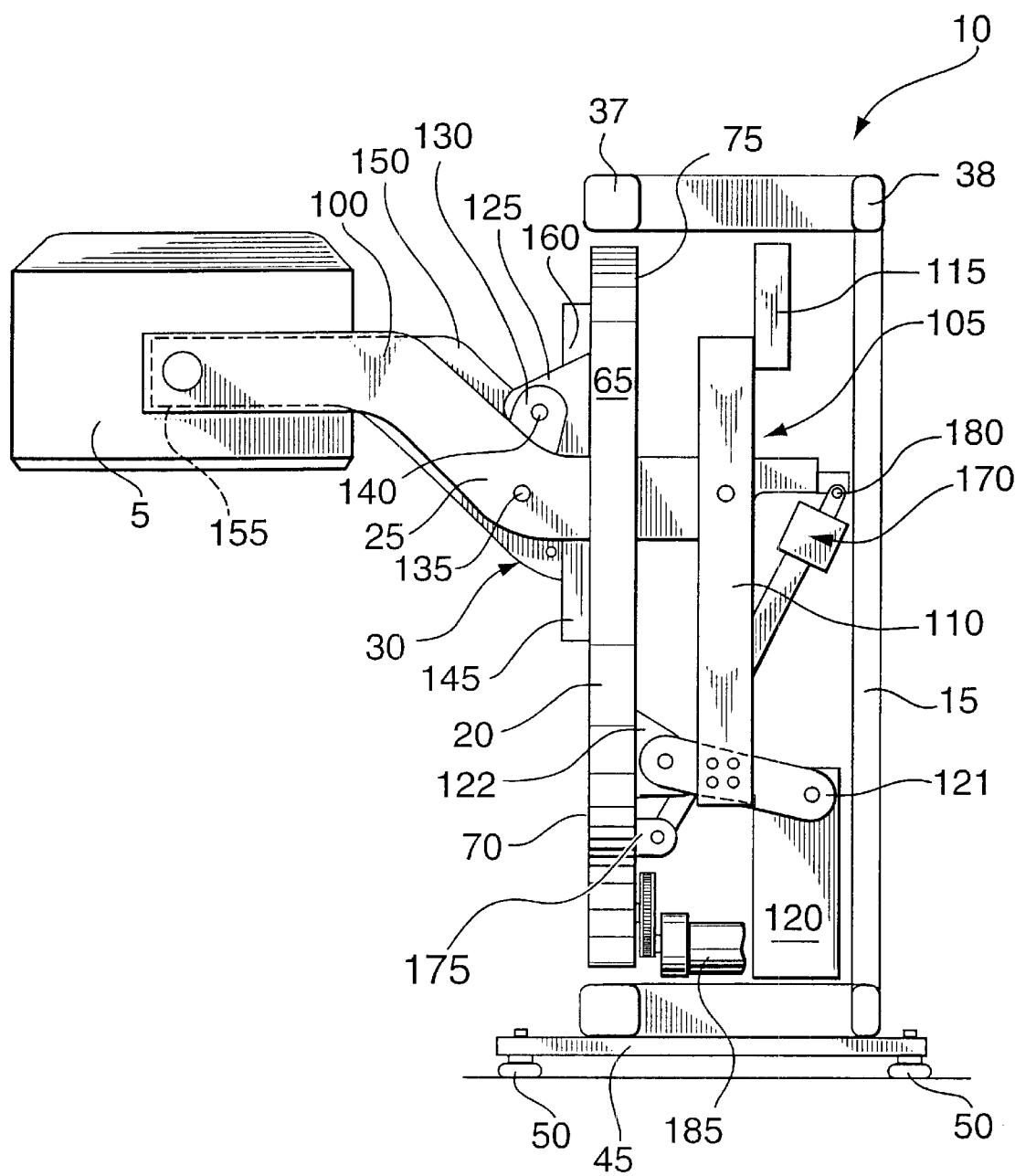
FIG. 4 is a side elevation view of a scintillation camera.
Figure 5:
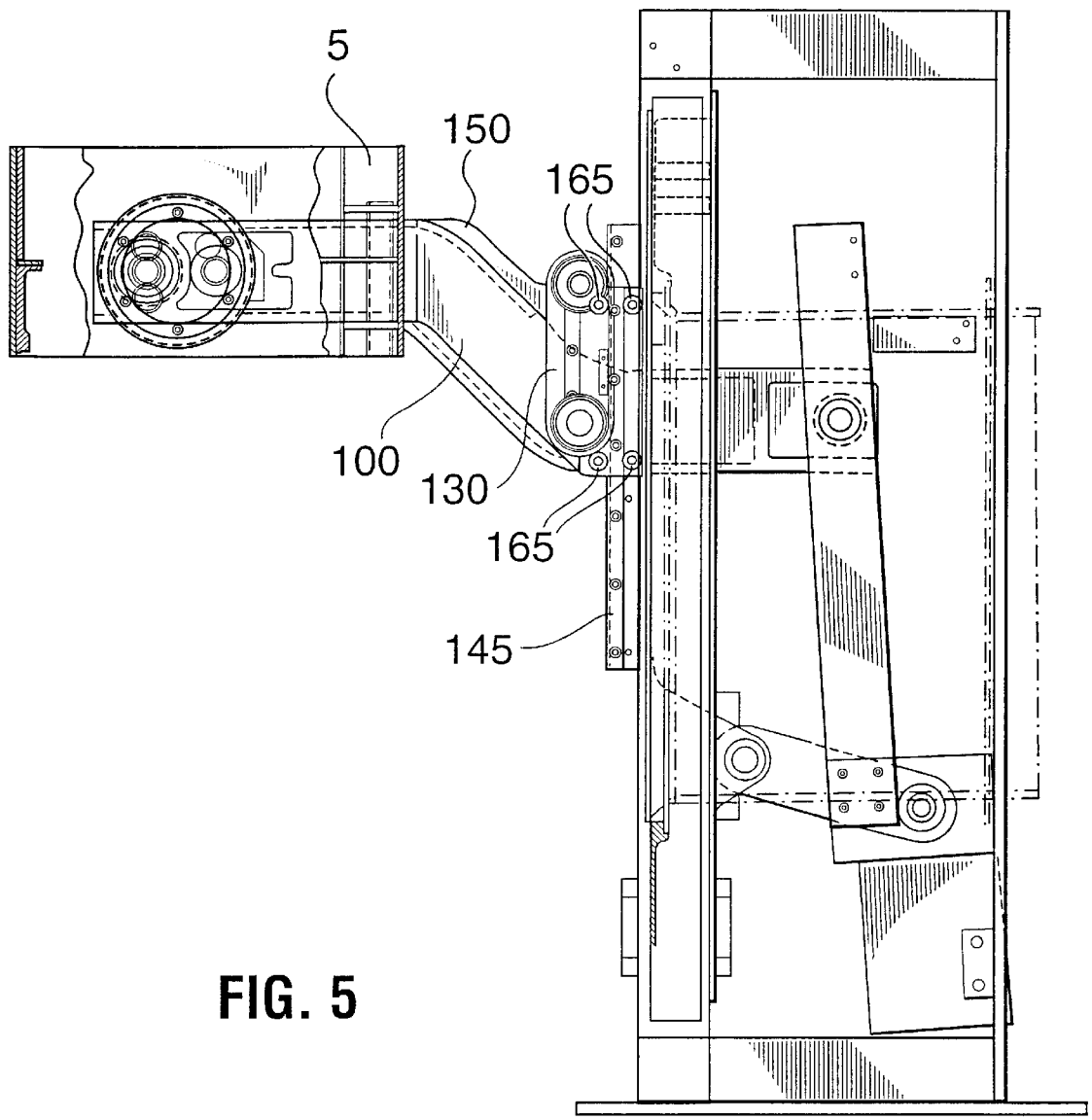
FIG. 5 is a side elevation view of a scintillation camera.
Figure 6:
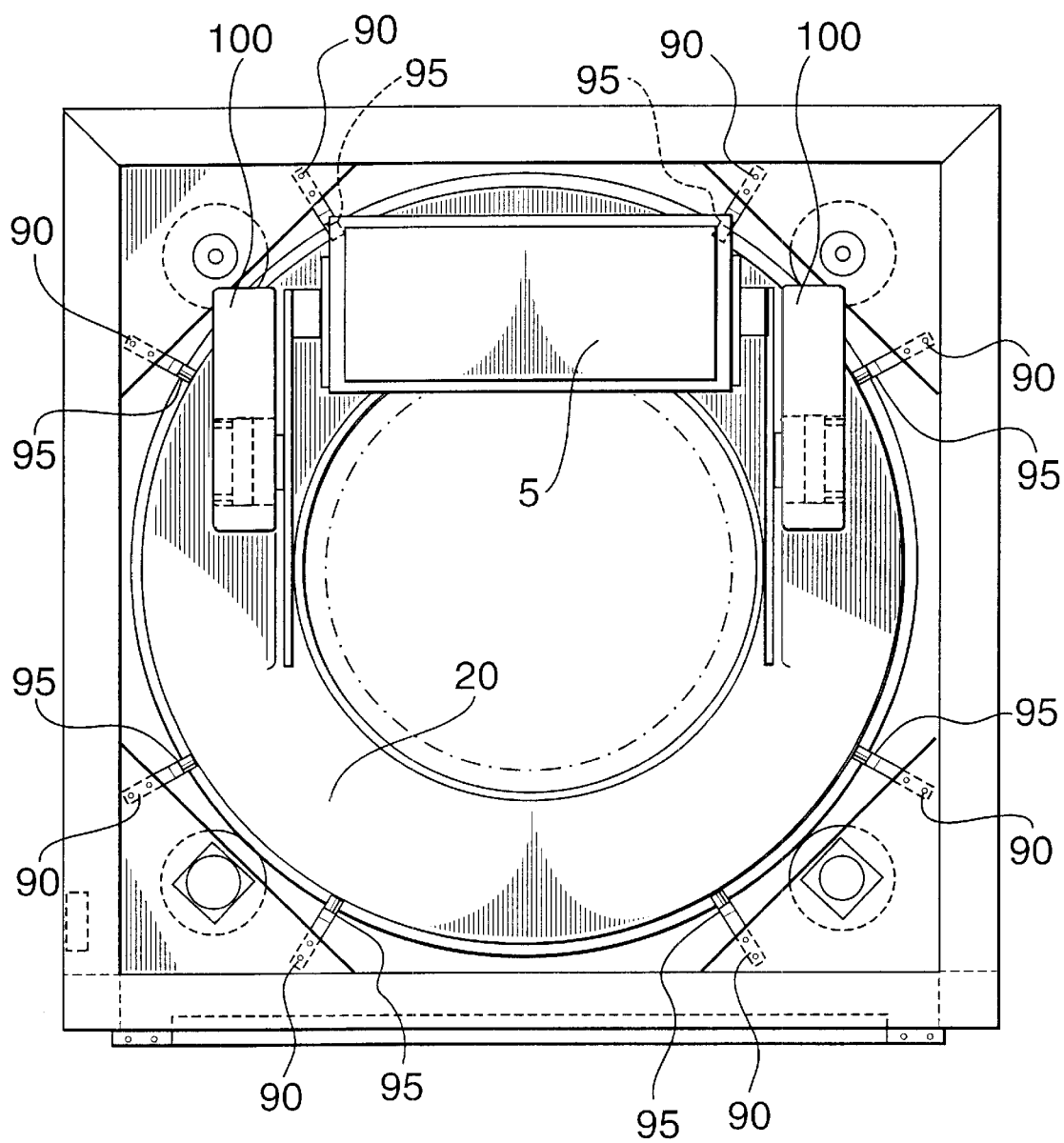
FIG. 6 is a front elevation view of a scintillation camera.
Figure 7:
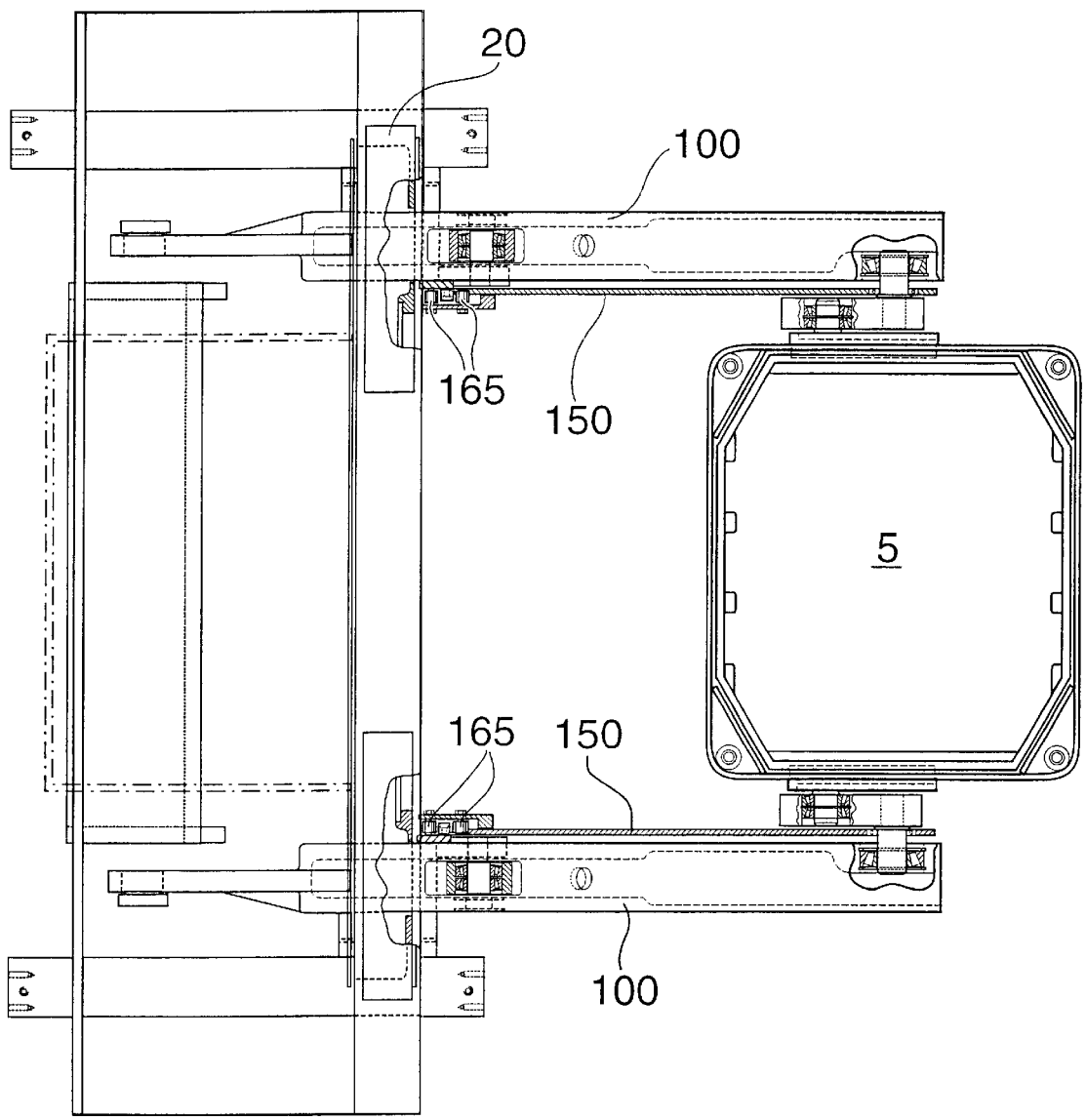
FIG. 7 is a top plan view of a scintillation camera.
Figure 8:
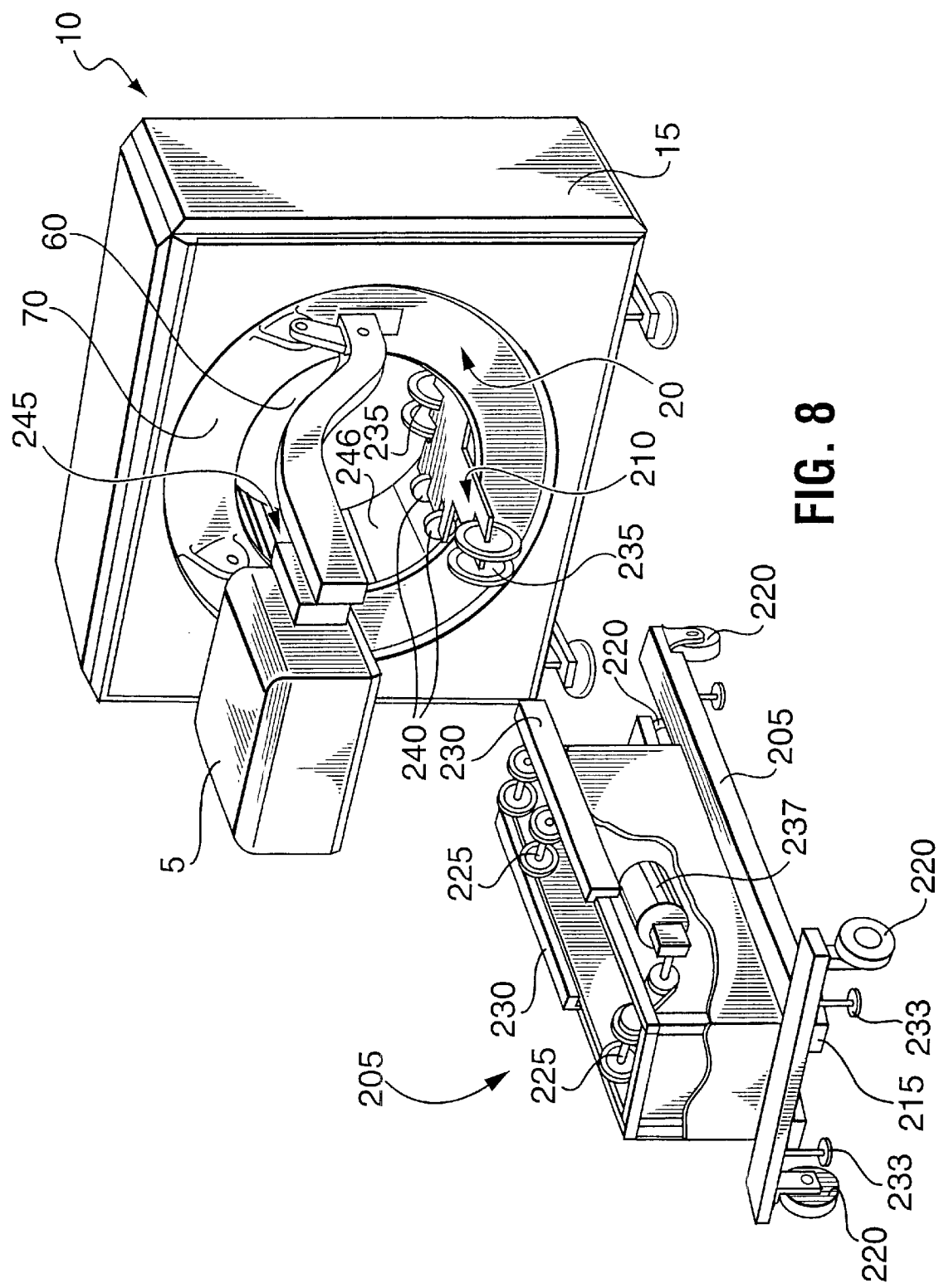
FIG. 8 is a perspective view of the scintillation camera of FIG. 1, including the detached patient support and engaged patient support, with the stretcher removed.
Figure 9:
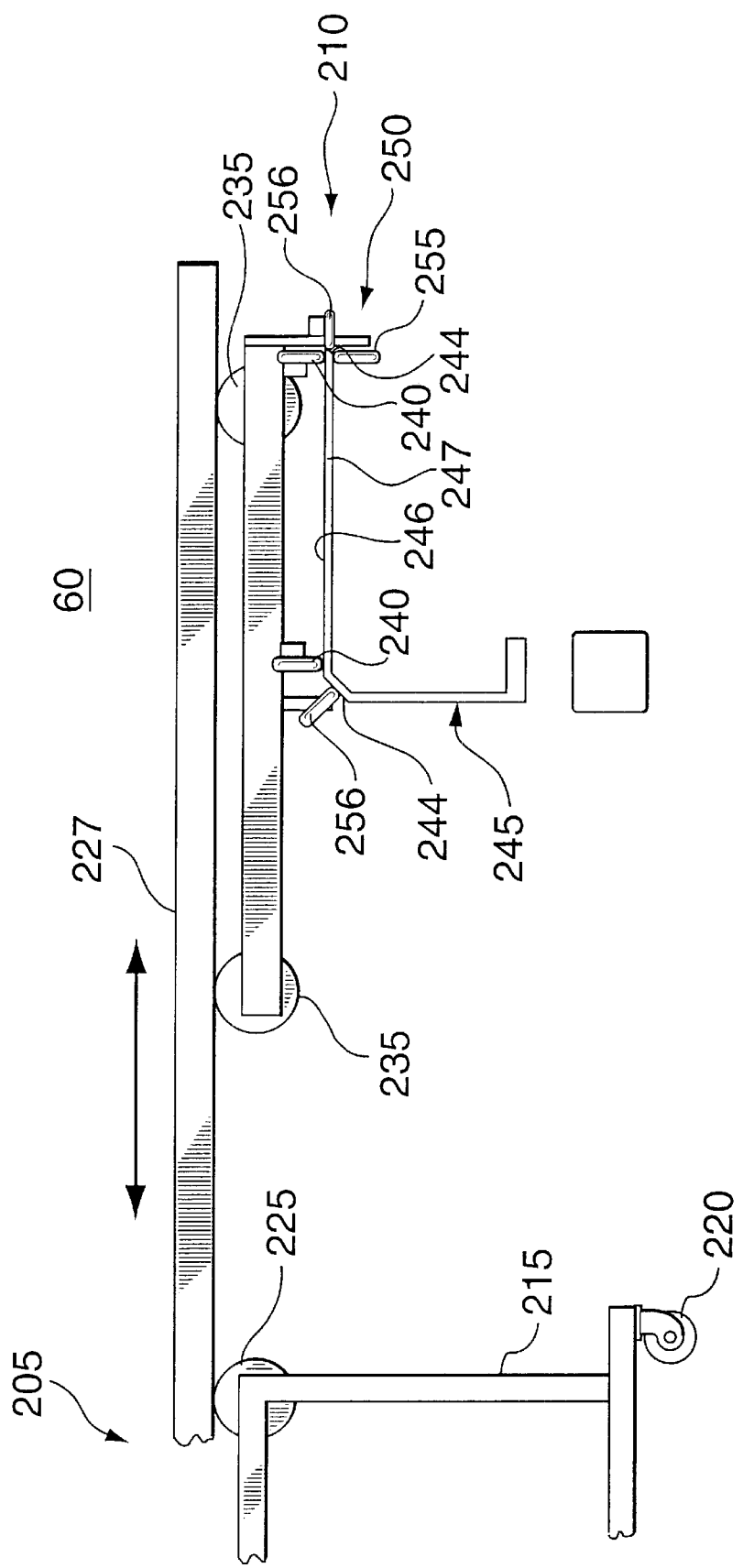
FIG. 9 is a side view of a portion of the patient support apparatus.
Figure 10:
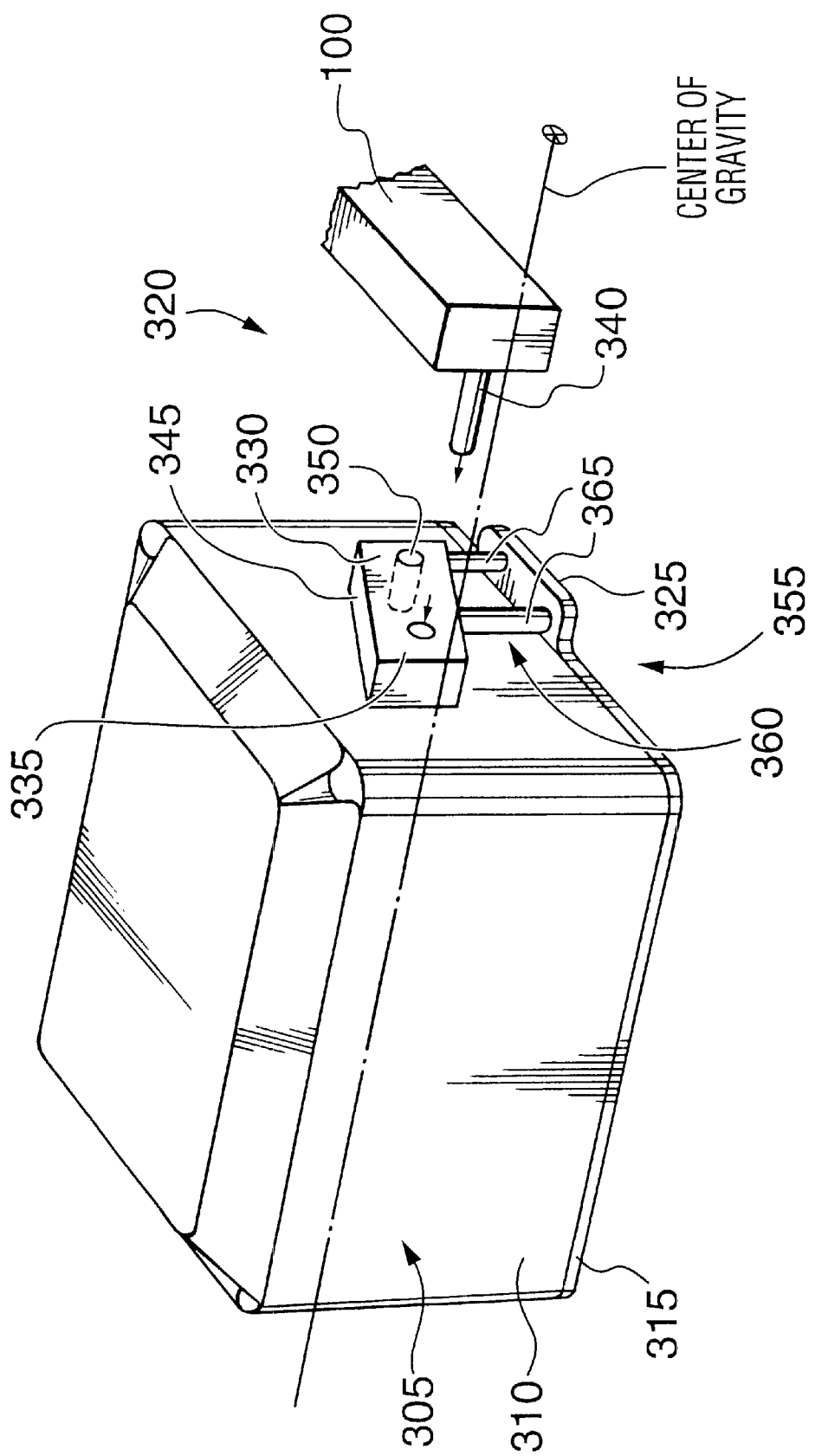
FIG. 10 is a perspective view of the positioner.
Figure 11:
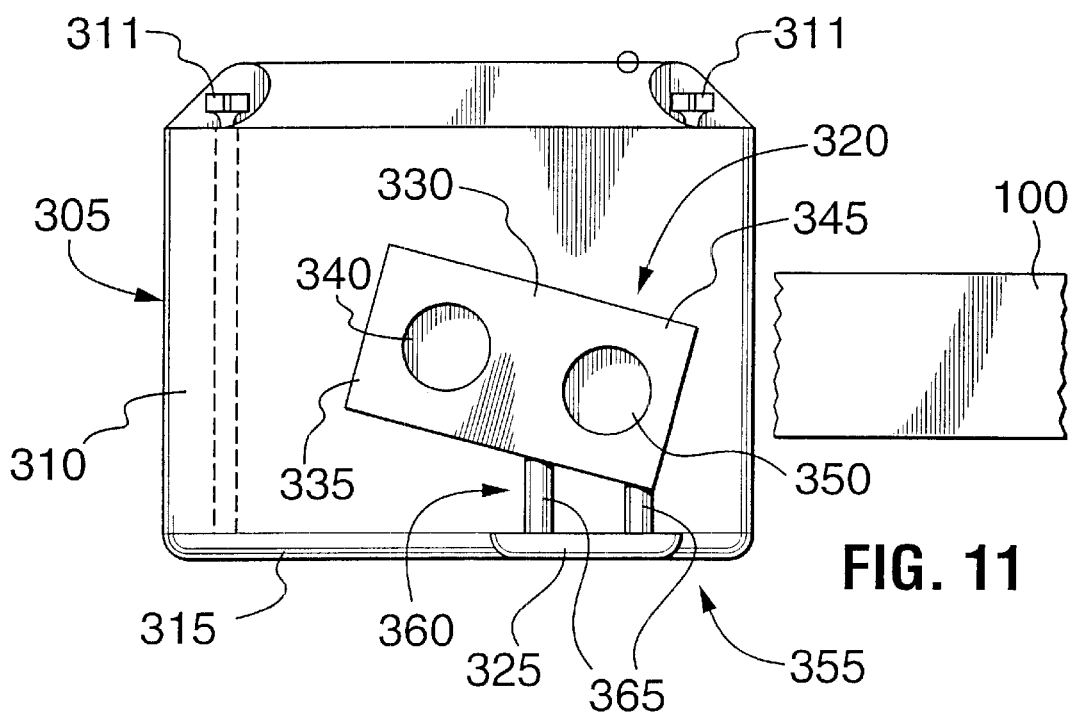
FIG. 11 is a side elevation view of the positioner.
Figure 12:
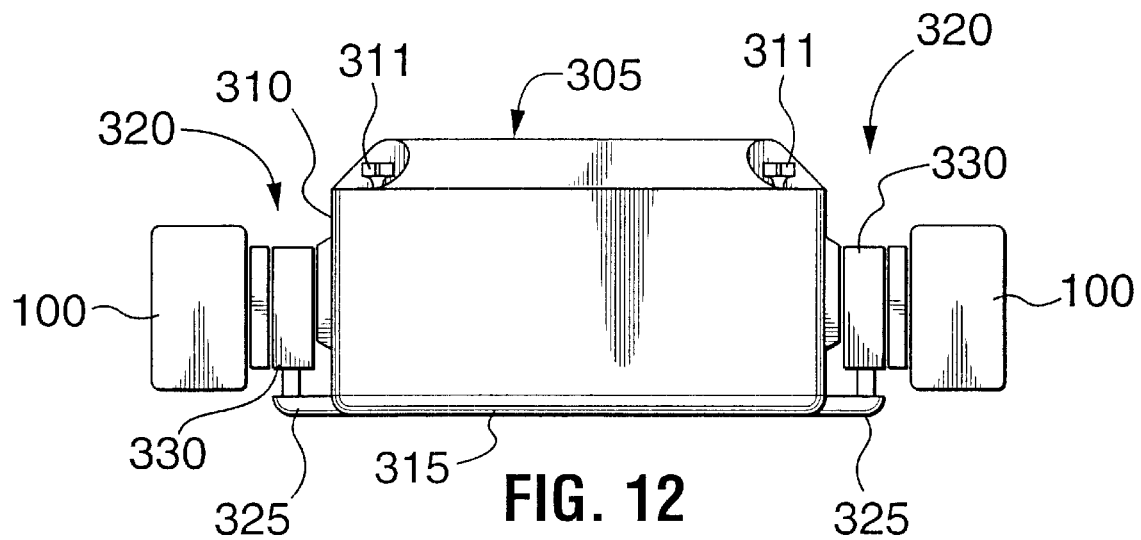
FIG. 12 is a front elevation view of the positioner.

Similar references are used in different figures to denote similar components.

DETAILED DESCRIPTION OF THE INVENTION

Referring to FIGS. 1 to 15, a nuclear camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30. and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. In the illustrated embodiment, the frame 35 is approximately five feet wide, five feet high, and two feet deep. The frame 35 also includes eight triangular corner braces 40 welded to the front square section 37, that is, each corner of the front square section 37 has two corner braces 40, one towards the front of the front square section 37, and one towards the rear of the front square section 37. In the illustrated embodiment, the corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. In the illustrated embodiment, the annular support 20 has an outside diameter of about fifty two inches. The annular support 20 is supported by upper rollers and lower rollers 85 which are mounted on the base 15. The upper rollers 80 and lower rollers 85 roll on the outer surface 65, thus enabling the annular support 20 to rotate relative to the base 15 in the plane defined by the annular support 20. Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 65 is adjustable. The curved surfaces of the upper rollers 80 and lower rollers 85 (i.e. the surfaces that contact the outer surface 65) should be tough so as to be able to withstand the pressures exerted by the annular support 20, and should have a fairly high coefficient of friction so as to roll consistently Attached to each pair of corner braces 40 is a stabilizing arm 90 oriented perpendicularly to the plane of the annular support 20. A pair of small stabilizing rollers 95 are mounted onto each stabilizing arm 90. Each pair of stabilizing rollers 95 is positioned such that one stabilizing roller 95 rolls on the front surface 70, and the other stabilizing roller 95 rolls on the rear surface 70. The stabilizing rollers 95 maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counter weight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counter weight member 110. Each counter weight link 121 is pivotally attached at its other end to a counter weight bracket 122 which is rigidly attached to the annular support 20. The counter weight links 121 are attached to the counterweight members 110 and counter weight brackets 122 using bolts and tapered roller bearings. Each counter weight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 of the illustrated embodiment is designed to operate with an apparatus for supporting and positioning a patient, such apparatus including a detached patient support 205, an engaged patient support 210, and a cylinder 245.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 245 is rigidly mounted to the annular support 20. The cylinder 245 is aligned with the orifice 60 of the annular support 20 such that the cylinder is coaxial with the annular support 20. The cylinder 245 includes a smooth inner surface 246 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 250. The stabilizer 250 includes outside wheels 255 to maintain the engaged patient support 210 horizontal, that is, to stop the engaged patient support from tipping relative to the cylinder 245. The outside wheels 255 roll on the outside surface 243 of the cylinder 245. The stabilizer 250 also includes end wheels 256 to prevent the engaged patient support 210 from moving in a direction parallel to the axis of the cylinder 215. The end wheels 256 roll on the ends 244 of the cylinder 245.

A detector head 305 of the nuclear camera 5 is supported between the two support arms 100 by a positioner 320. The detector head 305 includes a casing 310 in which is contained a scintillation crystal and photomultiplier tubes. Attached to the underside of the casing 310 is a collimator plate 315. The collimator plate 315 is made of lead perforated by narrow channels and includes a collimator support 325 extending from the two edges of the collimator plate adjacent the support arms 100. The collimator plate 315 is attached to the casing 310 by way of bolts 311. By removing the bolts 311, the collimator plate 315 can be removed from the casing 310 and replaced by another collimator plate 315. A particular design and weight of collimator is selected depending on the isotope being used or the type of study being conducted. Thus, the collimator plate 315 must be changed from time to time. Since the collimator plates 315 vary considerably in weight from one to another, the location of center of gravity of the detector head 305 is dependent upon the weight of the collimator plate 315 attached to the casing 310. Since the angle of the detector head 305 relative to the patient must be adjusted by an operator of the nuclear camera 5, the detector head 305 must be rotatable relative to the arms 100. If the center of gravity of the detector head 305 is positioned approximately on the axis of rotation of the detector head relative to the support arms 100, then the detector head 305 will be balanced, and the angle of the detector head 305 relative to the support arms 100 will be adjustable by hand. However, changing the collimator plates moves the center of gravity of the detector head. Since collimator plates 315 are so heavy, it becomes inconvenient or impossible to adjust the angle of the detector head 305 by hand. The positioner 320 enables the operator to adjust the position of the center of gravity of the detector head 305 to be approximately aligned with the point of rotation if the detector The positioner 310 attaches the detector head 305 to the support arms 100 and includes a pair of rigid elongate detector head links 330 for aligning the centre of gravity of the detector head 305 relative to the support arms 100. Each detector head link 330 is rotatable relative to the support arms 310 in a plane substantially parallel to its adjacent support arm 310. Each detector head link 330 includes an arm end 335 rotatably attached to the adjacent support arm 100 by way of an arm axle 340. Each detector head link 330 also includes a head end 345 rotatably attached to the detector head 305 by way of a head axle 350.

The positioner 310 also includes a pair of locks 355 for selectively preventing rotation of the detector head 305 relative to the detector head links 330. Each lock 355 includes the collimator support 325 extending from the detector head 305 from the collimator plate 315. Each lock 355 also includes a block 360 for supporting the detector head link 330 on the collimator support 325. Each block 360 includes a pair of pins 365 located either side of the head axle 350.

As discussed above, a scintillation camera has a planar scintillating crystal that produces light flashes whose spatial distribution corresponds to the spatial distribution of the radiation stimuli causing such events, and a plurality of photomultiplier tubes having photocathodes for receiving the light from the crystal through a planar face thereof. The application of a data reduction system enables the output of each photomultiplier tube to be digitized to high precision and provides data within the capacity of the computing means at high data rates. The computing means coupled to the photomultiplier tubes calculates the position of each light flash based on intensity values from at least three tubes. The control of the data converters to select the electrical signals that are required for the spatial calculation is performed to reduce the number of electrical signals transferred to the computing means.

Figure 13:
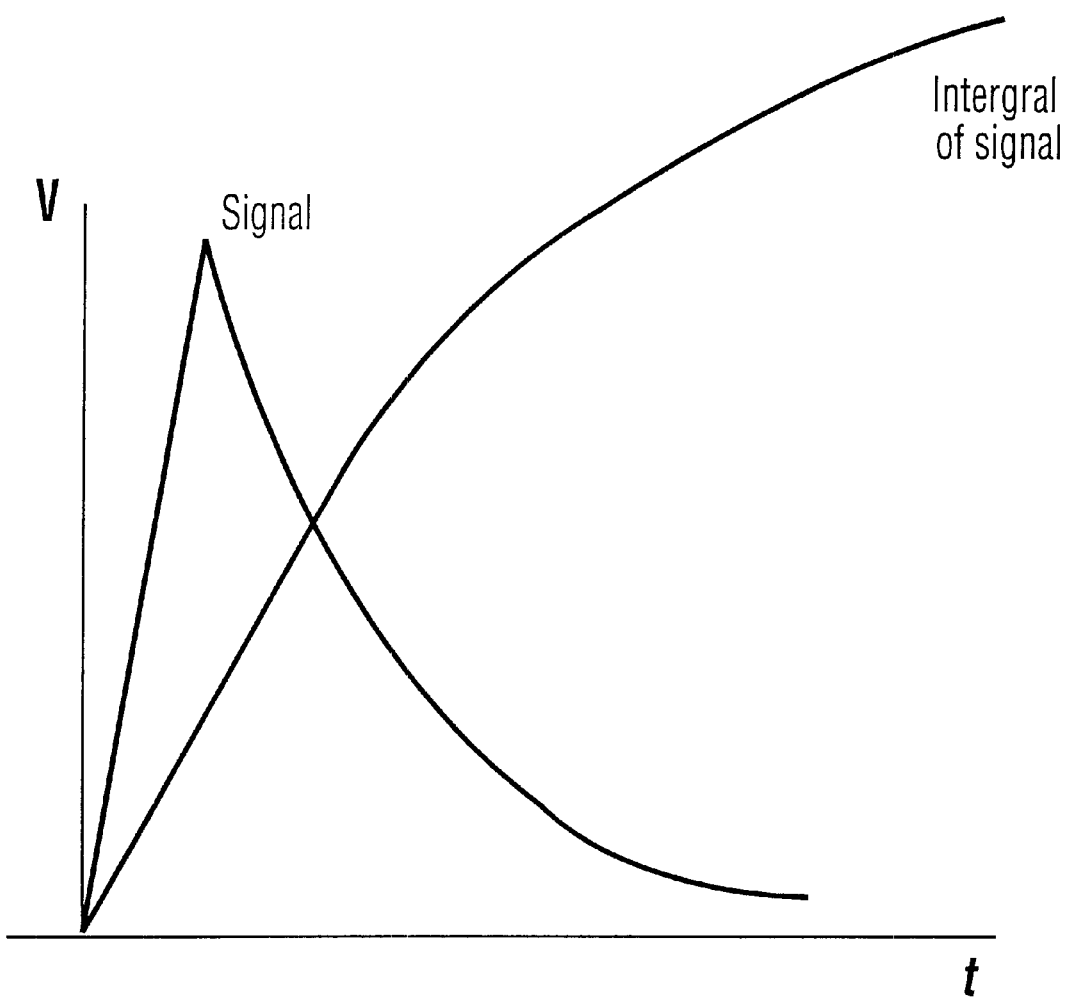
FIG. 13 illustrates two functions relating to the present invention.

In an embodiment of the invention, the signal uses a delayed differentiator which detects a change in slope and implements a circuit to perform an integration. See FIG. 13, which illustrates a trigger in accordance with the invention. The functions illustrated in FIG. 13 are labelled as the signal and the integral of the signal with the result that none of the signal is lost, as with an offset.

During the integration of the signal, the signal is also taken into the summing circuits, which add the signals in columns and rows. Comparators are then used to determine the largest column and row. These signals are then passed through an energy analyser to ensure that they are the result of a gamma event. Then the X and Y values are provided to a map that decides which tubes surround the largest column and row. Depending on the results, the signals that are being integrated are either selected or ignored. Only the selected integral values are then digitized. In other words, during the integration of a signal, the signal is used to locate an x and y location for the largest column and row, an energy analyser ensures that the signal is the result of a gamma event, the map is used to determine which signals to select, and selected integrated signals are digitized.

The result is a low cost data reducer for a scintillation camera that effectively selects signals from photomultiplier tubes while minimizing distortion of the signals.

Figure 14:
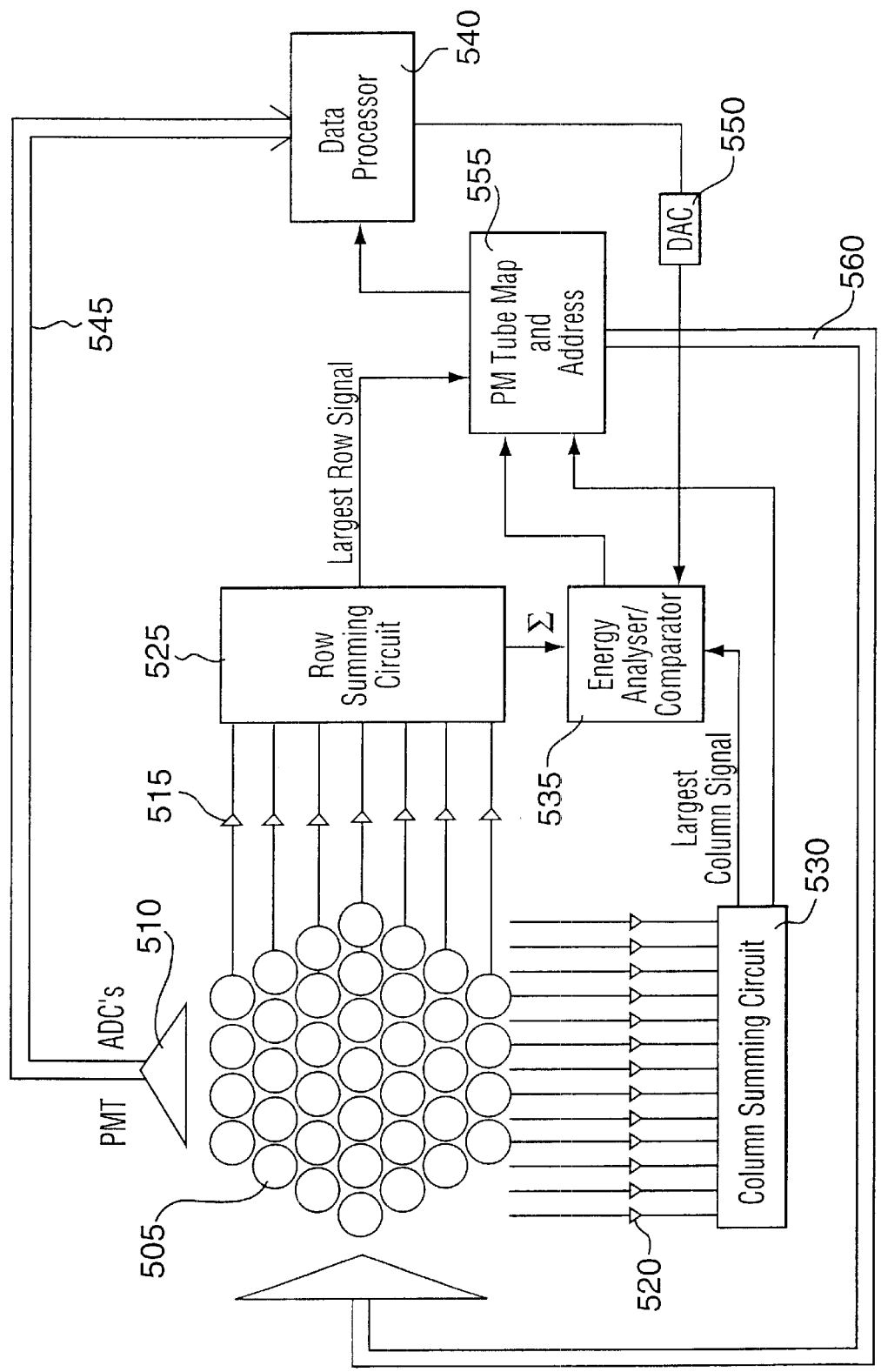
FIG. 14 is a drawing of an embodiment of a data reducer of the invention.
Figure 15:
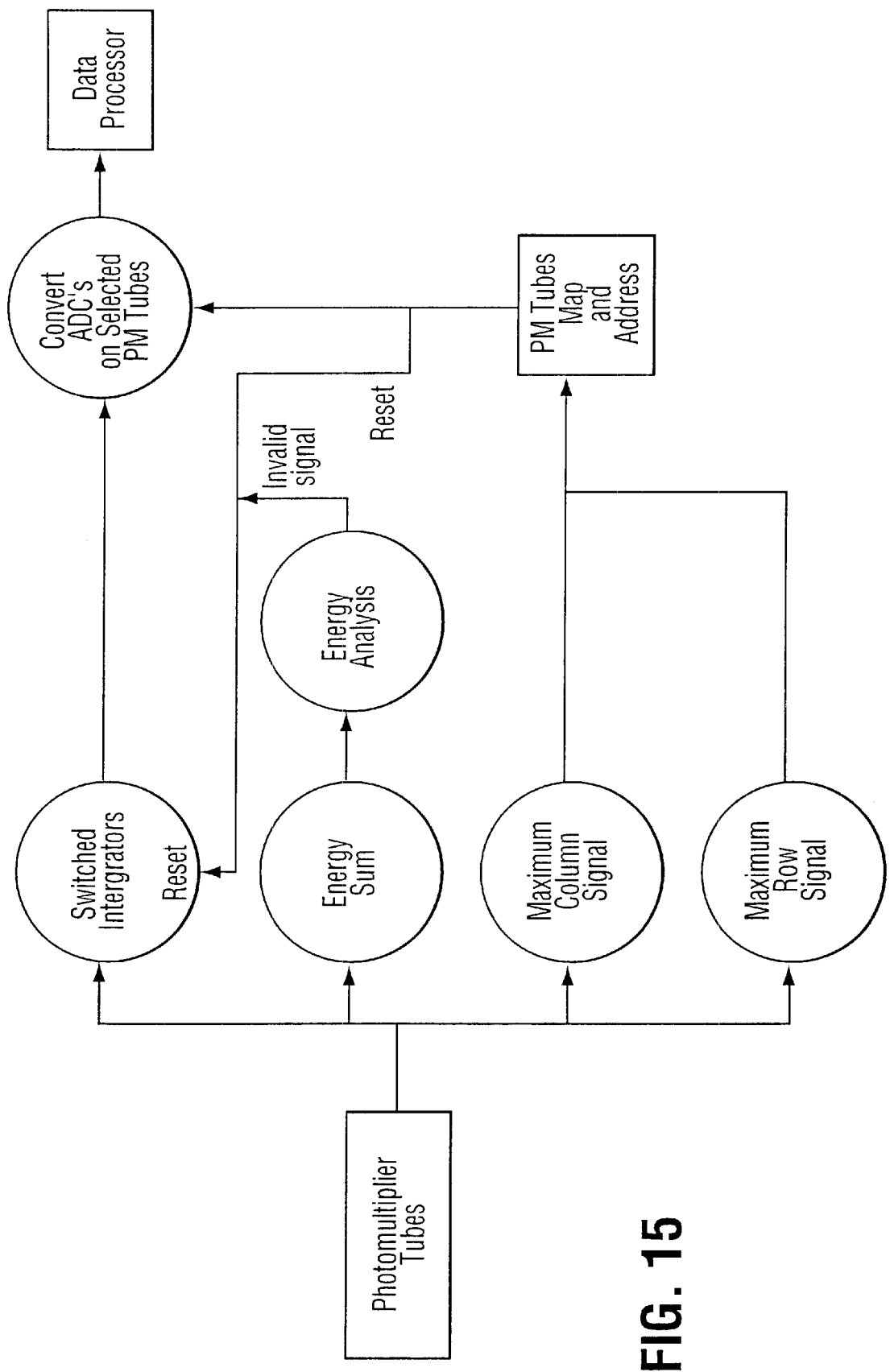
FIG. 15 is a diagram illustrating an embodiment of the method of the invention.

Referring to FIGS. 14 and 15, each photomultiplier tube 505 in the array thereof generates output signals following a flash of light from the scintillator. The output signal from a given photomultiplier tube 505 is connected to an integrating preamplifier circuit. Each output signal is connected to an analog to digital converter 510, to a row amplifier circuit 515 and to a column amplifier circuit 520.

The signal from the analog to digital converter 510 is provided via a first bus 545 to a data processor 540. The output signal of the data processor 540 is set according to operational requirements, and then provided to a digital to analog converter 550.

The signal from the row amplifier circuit 515 is provided to a row summing circuit 525 The signal from the column amplifier circuit 520 is provided to a column summing circuit 530. The respective signals from the row summing circuit 525 and the column summing circuit 530 are provided to an energy analyser 535. The energy analyser 535 ensures that the signal is the result of a gamma event and not, for example, from a cosmic ray or from scatter.

The output of the digital to analog converter 550 is compared with the output of the energy analyser 535. If the signal from the energy analyser 535 conforms with the requirements of the digital to analog converter 550, then a valid signal is sent to the photomultiplier tube map and address 555. From the row summing circuit 525 the largest row signal is sent to the photomultiplier tube map and address 555, and from the column summing circuit 530 the largest column signal is sent to the photomultiplier tube map and address 555.

In the majority of cases, the largest signal will be in a single row and column, and the output from that row and column will be transferred to the photomultiplier tube map and address 555. The output of the photomultiplier tube map and address 555 is connected to all the analog to digital converters 510 via the second bus 560. The analog to digital converters 510 convert the analog integrated signal into digital data for transmission to the data processor 540 via the first bus 545 for computation of the position of the light flash. The photomultiplier tube map and address 555 outputs the addresses of only the analog to digital converters 510 required to perform data conversion for transmission to the data processor 540. If the integrators are not included in the map, their values are rejected and the analog to digital converters 510 do not convert the values of the integrators into digital signals. If the light event occurs between two rows or columns, the two largest rows (from the row summing circuit 525) and the two largest columns (from the column summing circuit 530) will give an appropriate output signal. This special condition is interpreted by the photomultiplier tube map and address 555 and provides an enlarged conversion signal which allows a larger number of analog to digital converters 510 to convert their data, thus eliminating information loss or bias.

It should be noted that the signals from all the photomultiplier tubes in a row are added together. Thus, if the value for one row is larger than the value for an adjacent row, then the gamma event must have occurred somewhere along the row with the larger value. If two rows generate equal readings, then it may be assumed that the event occurred between the two rows. It does not matter whether one row has more photomultiplier tubes than another. If two event occur simultaneously, then the energy analyser will reject the event. That is, any events that occur close to simultaneously, will be discarded, as the composite energy signal will be greater than the energy signal from the gamma ray being examined. A similar analysis is performed with respect to the columns. This analysis is carried out at the same time as the integration process.

In an alternative embodiment, the summed energy signal is analyzed, in addition to the energy analyser, by a constant fraction discriminator which provides a valid signal on determining that the input signal from another detector is in time coincidence with the signals detected in the detector head.

Numerous modifications, variations and adaptations may be made to the particular embodiments of the invention described above without departing from the scope of the invention, which is defined in the claims.

I claim:

1. A method of reducing data in the localization processing of scintillation events in a scintillation camera having a plurality of photomultiplier tubes arranged in rows and columns, the method comprising steps of:

summing output signals from the photomultiplier tubes of each row to provide a summed row signal for each row;

summing output signals from the photomultiplier tubes of each column to provide a summed column signal for each column;

selecting a largest summed row signal and a largest summed column signal from the summed row and column signals; and selecting a subset of the plurality of photomultiplier tubes of which output signals are used for computing the location of a scintillation event, the subset of photomultiplier tubes comprising at least three photomultiplier tubes adjacent to both a row and a column corresponding to said largest summed row and column signals respectively, thereby reducing the amount of data to be processed for localizing scintillation events.

2. A method of claim 1, wherein said step of selecting a subset of the plurality of photomultiplier tubes comprises steps of:

locating an X location and a Y location corresponding to said largest summed row and summed column signals;

providing the addresses corresponding to the subset of the photomultiplier tubes, which surround the X and Y locations; and selecting, based on the addresses, the output signals of the subset of the photomultiplier tubes to compute the location of the scintillation event.

3. A method of claim 1, further comprising the step of digitizing the output signals of the subset of the photomultiplier tubes.

4. A method of claim 1, further comprising the step of determining if each of the summed row and column signals is the result of a gamma event.

5. An apparatus for reducing data in the localization processing of scintillation events in a scintillation camera having a plurality of photomultiplier tubes arranged in rows and columns, the apparatus comprising:

a first summing circuit for summing output signals from the photomuliplier tubes of each row to provide a summed row signal for each row;

a second summing circuit for summing output signals from the photomultiplier tubes of each column to provide a summed column signal for each column;

means for selecting a largest summed row signal and a largest summed column signal from the summed row and column signals; and means for selecting a subset of the plurality of photomultiplier tubes of which output signals are used for computing the location of a scintillation event, the subset of photomultiplier tubes comprising at least three photomultiplier tubes adjacent to both a row and a column corresponding to said largest summed row and column signals respectively, thereby reducing the amount of data to be processed for localizing scintillation events.

6. The apparatus of claim 5, wherein said means for selecting a subset of the plurality of photomultiplier tubes comprises:

means for locating an X location and a Y location corresponding to said largest summed row and summed column signals and for providing the addresses corresponding to the subset of the photomultiplier tubes, which surround the X and Y locations; and means for selecting, based on the addresses, the output signals of the subset of the photomultiplier tubes to compute the location of the scintillation event.

7. The apparatus of claim 5, further comprising an analyser for determining if each of said summed row and column signals is the result of a gamma event.

8. The apparatus of claim 5, further comprising a converter for digitizing the output signals of the subset of the photomultiplier tubes to compute the location of the scintillation event.

* * * * *